(12) United States Patent
Wang et al.

(10) Patent No.: US 7,222,024 B2
(45) Date of Patent: May 22, 2007

(54) METHOD FOR DETERMINING THE CONCENTRATION OF BLOOD GLUCOSE

(76) Inventors: Kuo-Jeng Wang, 14, Kung-An St., Hsiao-Kang, Kaohsiung City (TW); Jian-Tsz Chen, 32, Lane 710, Sec. 1, Sha-Tien Rd., Ta-Du Hsiang, Taichung (TW)

( * ) Notice: Subject to any disclaimer, the term of this patent is extended or adjusted under 35 U.S.C. 154(b) by 280 days.

(21) Appl. No.: 10/410,292

(22) Filed: Apr. 10, 2003

(65) Prior Publication Data

US 2004/0126832 A1    Jul. 1, 2004

(30) Foreign Application Priority Data

Dec. 31, 2002    (TW) .............................. 91138108 A

(51) Int. Cl.
G06F 19/00 (2006.01)
H03M 1/00 (2006.01)
C12M 1/34 (2006.01)
C12Q 1/54 (2006.01)
C12Q 1/26 (2006.01)

(52) U.S. Cl. ............................ 702/23; 710/69; 435/14; 435/25

(58) Field of Classification Search .................. None
See application file for complete search history.

(56) References Cited

U.S. PATENT DOCUMENTS

| | | | |
|---|---|---|---|
| 3,837,922 A | 9/1974 | Ng et al. |
| 4,005,002 A | 1/1977 | Racine et al. |
| 4,129,478 A | 12/1978 | Racine et al. |
| 4,274,832 A | 6/1981 | Wu et al. |
| 4,299,493 A | 11/1981 | Harrison |
| 4,407,290 A | 10/1983 | Wilber |
| 4,407,959 A | 10/1983 | Tsuji et al. |
| 4,420,564 A | 12/1983 | Tsuji et al. |
| 4,444,743 A | 4/1984 | Yokoyama et al. |
| 4,689,309 A | 8/1987 | Jones |
| 4,772,561 A | 9/1988 | Genshaw |
| 4,791,066 A | 12/1988 | Ishiguro |
| 4,805,624 A | 2/1989 | Yao et al. |
| 4,850,805 A | 7/1989 | Madsen et al. |
| 4,861,771 A | 8/1989 | Gaitanopoulos et al. |
| 4,875,486 A | 10/1989 | Rapoport et al. |
| 4,891,104 A | 1/1990 | Liston et al. |
| 5,002,893 A | 3/1991 | Rosenthal |
| 5,198,367 A | 3/1993 | Aizawa et al. |
| 5,222,495 A | 6/1993 | Clarke et al. |
| 5,222,496 A | 6/1993 | Clarke et al. |
| 5,246,002 A | 9/1993 | Prosser |
| 5,284,845 A | 2/1994 | Paulsen |
| 5,332,803 A | 7/1994 | Miyazaki et al. |
| 5,337,745 A | 8/1994 | Benaron |
| 5,341,805 A | 8/1994 | Stavridi et al. |
| 5,344,832 A | 9/1994 | Cincotta et al. |
| 5,362,966 A | 11/1994 | Rosenthal et al. |
| 5,365,066 A | 11/1994 | Krueger, Jr. et al. |
| 5,370,114 A | 12/1994 | Wong et al. |
| 5,407,545 A | 4/1995 | Hirose |
| 5,420,108 A | 5/1995 | Shohet |
| 5,468,755 A | 11/1995 | Cincotta et al. |
| 5,494,562 A | 2/1996 | Maley et al. |
| 5,496,803 A | 3/1996 | Meier et al. |
| 5,500,374 A | 3/1996 | Wenzhi |
| 5,532,602 A | 7/1996 | Wiget |
| 5,554,623 A | 9/1996 | Cincotta et al. |
| 5,585,347 A | 12/1996 | Meier et al. |
| 5,592,086 A | 1/1997 | Weinstock et al. |
| 5,616,558 A | 4/1997 | Ohneda et al. |
| 5,700,776 A | 12/1997 | Ohneda et al. |
| 5,814,600 A | 9/1998 | Rink et al. |
| 5,882,935 A | 3/1999 | Hirai et al. |
| 6,011,984 A | 1/2000 | Van Antwerp et al. |
| 6,024,488 A | 2/2000 | Wu et al. |
| 6,091,976 A | 7/2000 | Pfeiffer et al. |
| 6,312,924 B1 | 11/2001 | Presnell et al. |
| 6,317,700 B1 | 11/2001 | Bagne |
| 6,350,431 B1 | 2/2002 | Snow et al. |
| 6,355,788 B1 | 3/2002 | Conklin et al. |
| 6,361,985 B1 | 3/2002 | Conklin et al. |
| 6,416,988 B1 | 7/2002 | Conklin et al. |
| 6,428,704 B1 | 8/2002 | Setoguchi et al. |
| 6,434,409 B1 | 8/2002 | Pfeiffer et al. |
| 2002/0133064 A1* | 9/2002 | Ueno et al. .................. 600/316 |
| 2003/0150724 A1* | 8/2003 | Kawanaka ............. 204/403.02 |
| 2004/0126832 A1 | 7/2004 | Wang |
| 2004/0210401 A1 | 10/2004 | Huang et al. |

FOREIGN PATENT DOCUMENTS

| | | |
|---|---|---|
| DE | 1422 172 | 1/1972 |
| TW | 091138108 | 12/2002 |
| WO | WO 0011205 | 3/2000 |

* cited by examiner

*Primary Examiner*—Marjorie A. Moran
(74) *Attorney, Agent, or Firm*—Berkeley Law & Technology Group

(57) ABSTRACT

The present invention provides a method for determining concentration of blood glucose by using the change in the rising time. The chemical reaction between the blood glucose and enzyme within the test strip to generate the analog source that used to determine the concentration of the blood glucose in the measuring meter. Thus, the rising curve can be obtained after the analog source is treated, such that the concentration of the blood glucose can be determined.

3 Claims, 4 Drawing Sheets

METHOD FOR DETERMINING THE CONCENTRATION OF BLOOD GLUCOSE

BACKGROUND OF THE INVENTION

1. Field of the Invention

The present invention generally relates to a method for determining the concentration of blood glucose, and more particularly to a method for determining the concentration of blood glucose by using the change in rising curve.

2. Description of the Prior Art

In the past, many systems have been developed for monitoring blood characteristics. For example, devices have been developed which are capable of determining such blood characteristics as blood oxygenation, glucose concentration, and other blood characteristics. However, significant difficulties have been encountered when attempting to determine blood glucose concentration accurately using noninvasive blood monitoring systems such as by means of spectroscopic measurement.

The difficulty in determining blood glucose concentration accurately may be attributed to several causes. One of the significant causes is that blood glucose is typically found in very low concentrations within the bloodstream (e.g., on the order of 100 to 1,000 times lower than hemoglobin) so that such low concentrations are difficult to detect noninvasively, and require a very high signal-to noise ratio. Additionally, with spectroscopic methods, the optical characteristics of glucose are very similar to those of water, which is found in a very high concentration within the blood. Thus where optical monitoring systems are used, the optical characteristics of water tend to obscure the characteristics of optical signal due to glucose within the bloodstream. Furthermore, since each individual has tissue, bone, and unique blood properties, each measurement typically requires calibration for the particular individual.

Test strips are known that contain a testing reagent that turns a different shade of color, depending on the concentration of glucose in a blood sample that has been applied to the strip. The blood glucose concentration is measured by inserting a strip into a meter that is basically a reflectance photometer, which determines the concentration from the change in color caused by the reaction between the testing reagent and blood glucose. The testing reagent typically contains an enzyme, such as glucose oxidase, which is capable of oxidizing glucose to gluconic acid lactone and hydrogen peroxide; and oxidizable dye; and a substance having peroxidative activity, which is capable of selectively catalyzing oxidation of the oxidizable dye in the presence of hydrogen peroxide.

In the conventional measuring meter, the measuring time is usually of about 10 to 30 seconds, which is too long to obtain an exact concentration of the blood glucose, when the concentration of the blood glucose is determined by sampling the data that is basically a fixed sampling time.

SUMMARY OF THE INVENTION

It is an object of this invention that a method for determining the concentration of the blood glucose by performing the rising curves.

It is another object of this invention that a method for calculating the concentration of the blood glucose by utilizing a change in rising curves.

It is yet another object of this invention that a method for creating mapping table from rising time and concentration of the blood glucose to determine the unknown concentration of the blood glucose.

According to above-mentioned objects, the present invention provides a method to determine the concentration of the blood glucose by using the change in the rising curve. The blood glucose is reacted with the enzyme within the test strips to generate the analog source, and the analog source is inserted into the measuring meter to measure the concentration of the blood glucose, and the rising curve also can be obtained. Because of the rising time of the rising curve is very short the exact concentration of the blood glucose can be obtained immediately.

BRIEF DESCRIPTION OF THE DRAWINGS

The foregoing aspects and many of the attendant advantages of this invention will become more readily appreciated as the same becomes better understood with reference to the following detailed description, when taken in conjunction with the accompanying drawings, wherein.

DESCRIPTION OF THE PREFERRED EMBODIMENT

Some sample embodiments of the invention will now be described in greater detail. Nevertheless, it should be recognized that the present invention can be practiced in a wide range of other embodiments besides those explicitly described, and the scope of the present invention is expressly not limited except as specified in the accompanying claims.

According to the conventional determining method, the time to determine the concentration of blood glucose is of about 10 to 30 seconds, that is too long to increase the inaccuracy in concentration estimation. Thus, the present invention provides a method for determining the concentration of blood glucose by utilizing the rising curve to estimate the exact the concentration.

Figure 1:
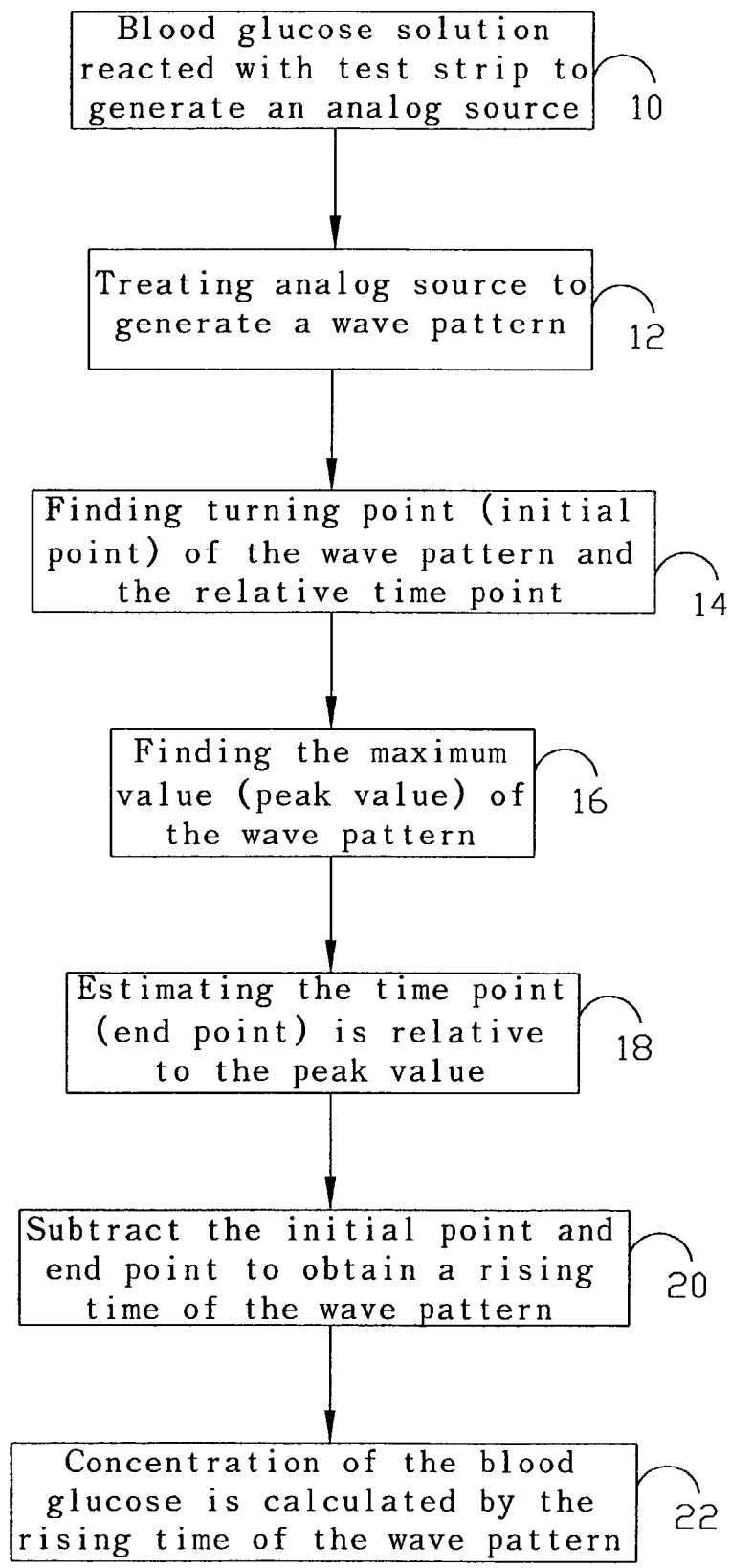
FIG. 1 is a flow chart showing the step for determining the concentration of the blood glucose immediately in accordance with a method disclosed herein.

Referring to FIG. 1, FIG. 1 is a flow chart showing the steps for determining the concentration of the blood glucose by using the rising curve. Step 10 indicates the blood glucose may react with the enzyme within the test strip to generate the analog source; step 12 indicates the treatment device may be used to treat the analog source to convert the analog source from the analog signal into the digital signal, and that the wave pattern is displayed by an outputting device, wherein the wave pattern represents the relationship between the concentration of the blood glucose and rising time. In accordance with the present invention, the outputted signal is represented by voltage; wherein the unit of the voltage is milli-volt (mv.)

Then, the turning point is found from the wave pattern, and the time can be found which is relative to the turning point, wherein the turning point may be named the initial point (step 14.) Next, the maximum value is found from the wave pattern, wherein the maximum value of the wave pattern is the peak value (step 16.) Thereafter, the time point relative to the peak value of the wave pattern can be estimated, wherein the time point relative to the peak value is the end point (step 18;) next, the difference value between the initial point and end point is estimated by subtracting the initial point and the end point, wherein the difference value is the rising time (step 20;) and finally, a relative diagram is constructed by the concentration of the blood glucose and the rising time. Therefore, when the unknown concentration of the blood glucose is inserted into the measuring meter, the concentration of the blood glucose can be obtained immediately from the relative diagram (step 22.)

Figure 2:
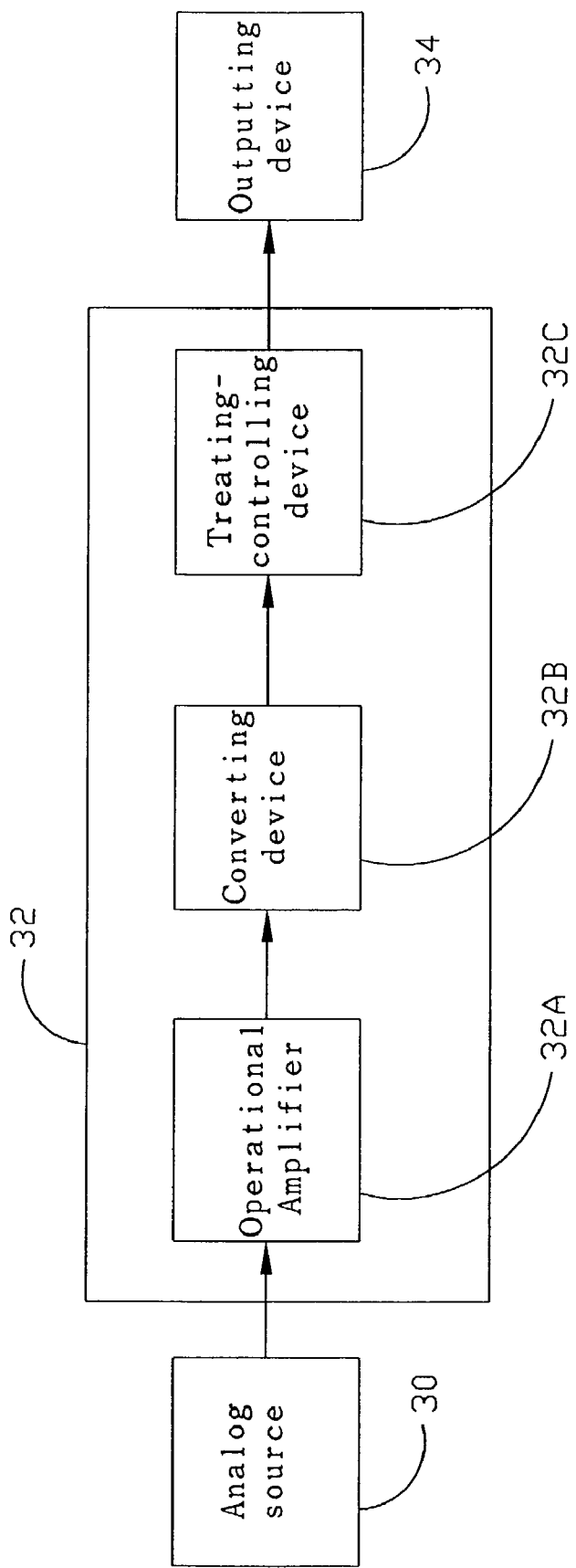
FIG. 2 is a block diagram showing the step for determining the concentration of the blood glucose by using the rising curve in accordance with a method disclosed herein.

Furthermore, FIG. 2 is a block diagram showing the steps for determining the concentration of the blood glucose. The reference character 30 denotes the analog source, wherein the analog source is generated by the chemical reaction between the blood glucose and the enzyme within the test strip, and the chemical reaction is an oxidation-reduction reaction. Then, the analog source is inputted into a treatment device 32 to convert the analog source from the analog signal into a digital signal. The treatment device 32 comprises an operational amplifier 32A, a converting device 32B, and a treating-controlling device 32C. The operational amplifier 32A may be used to transfer the analog signal into the converting device 32B, and the converting device 32B may convert the analog signal into the digital signal, wherein the converting device 32B can be an AFE (analog-front-end) device or ADC (analog-to-digital converting system), and the treating-controlling device 32C is a MCU (microprocessor control unit). Then, the digital signal is displayed by a wave pattern shape in an outputting device 34.

Figure 3:
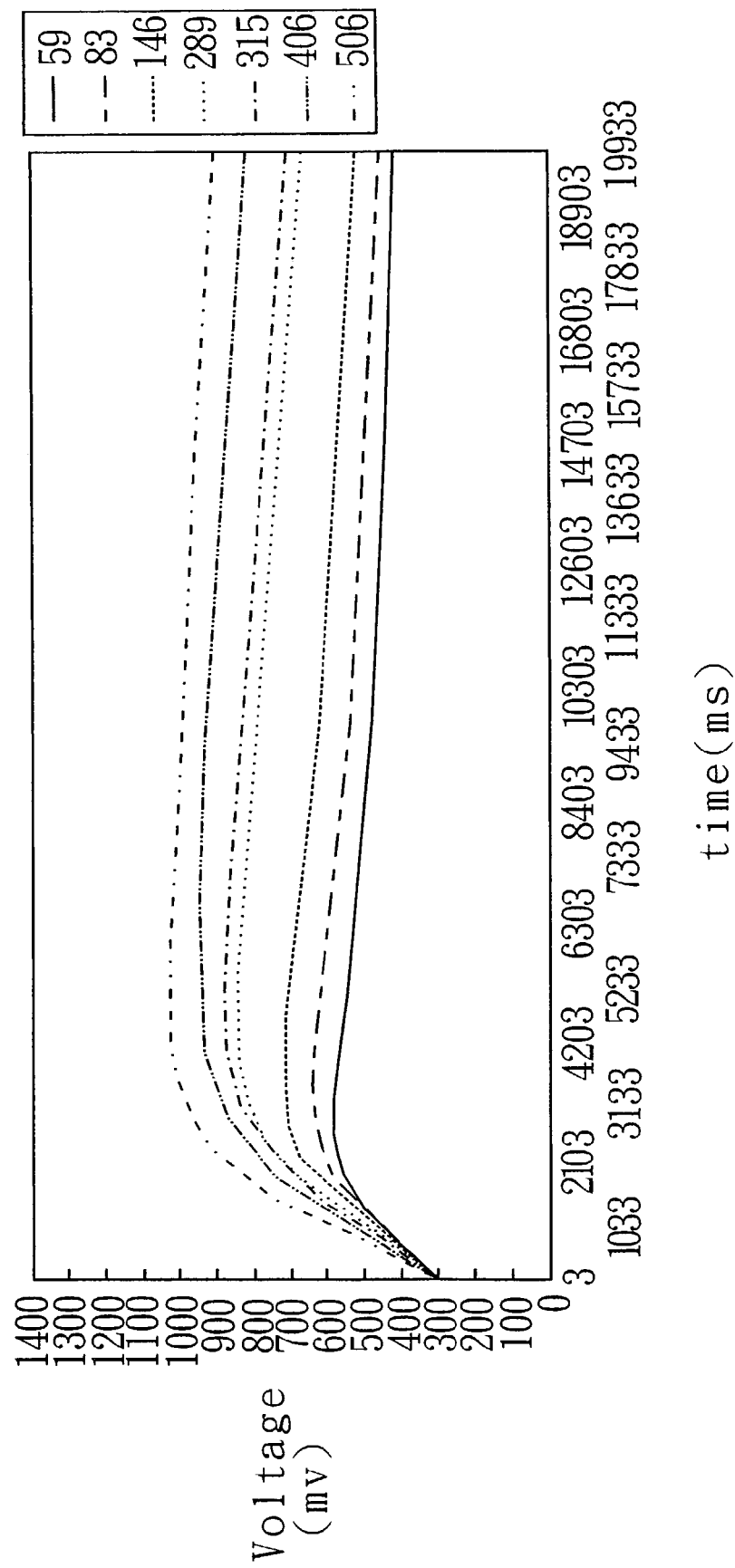
FIG. 3 is schematic representation showing the wave pattern for different concentration of the blood glucose that after treatment in accordance with a method disclosed herein.

Then, the FIG. 3 shows a wave pattern for the different concentration of the blood glucose and the reaction time, wherein the x-coordinate is reaction time, the unit is millisecond (ms), and the y-coordinate is outputted voltage, the unit is milli-volt (mv). Thus, the reaction time of the rising curve will become longer when the blood glucose has a higher concentration, so that the concentration of the blood glucose can be determined by the reaction time of the rising curve.

The preferred embodiment of the present invention provides a method to estimate the different concentration of the blood glucose. First, the turning point of the rising curve can be found, and the time point relative to the turning point of the rising curve also can be found, wherein the turning point is an initial point or first time. Then, according to the value of the first order differential greater than the zero, the maximum value of the each concentration of the blood glucose can be found, and the time point relative to the maximum value also can be found, herein the time point is the end point or second time. Next, the difference value between the initial point and end point is estimated by subtracting the initial point and the end point, wherein the difference value is the rising time of the rising curve.

In accordance with the present invention, the rising time is very short and could determine the concentration of the blood glucose immediately. Therefore, the exact concentration value can be estimated by the change in the rising time. To compare the estimating time between the conventional measuring meter and the rising time of the present invention, this invention only needs about 5 seconds to obtain the exact concentration of the blood glucose, nevertheless, the conventional measuring meter requires more than 10 seconds to obtain the concentration of blood glucose.

Figure 4:
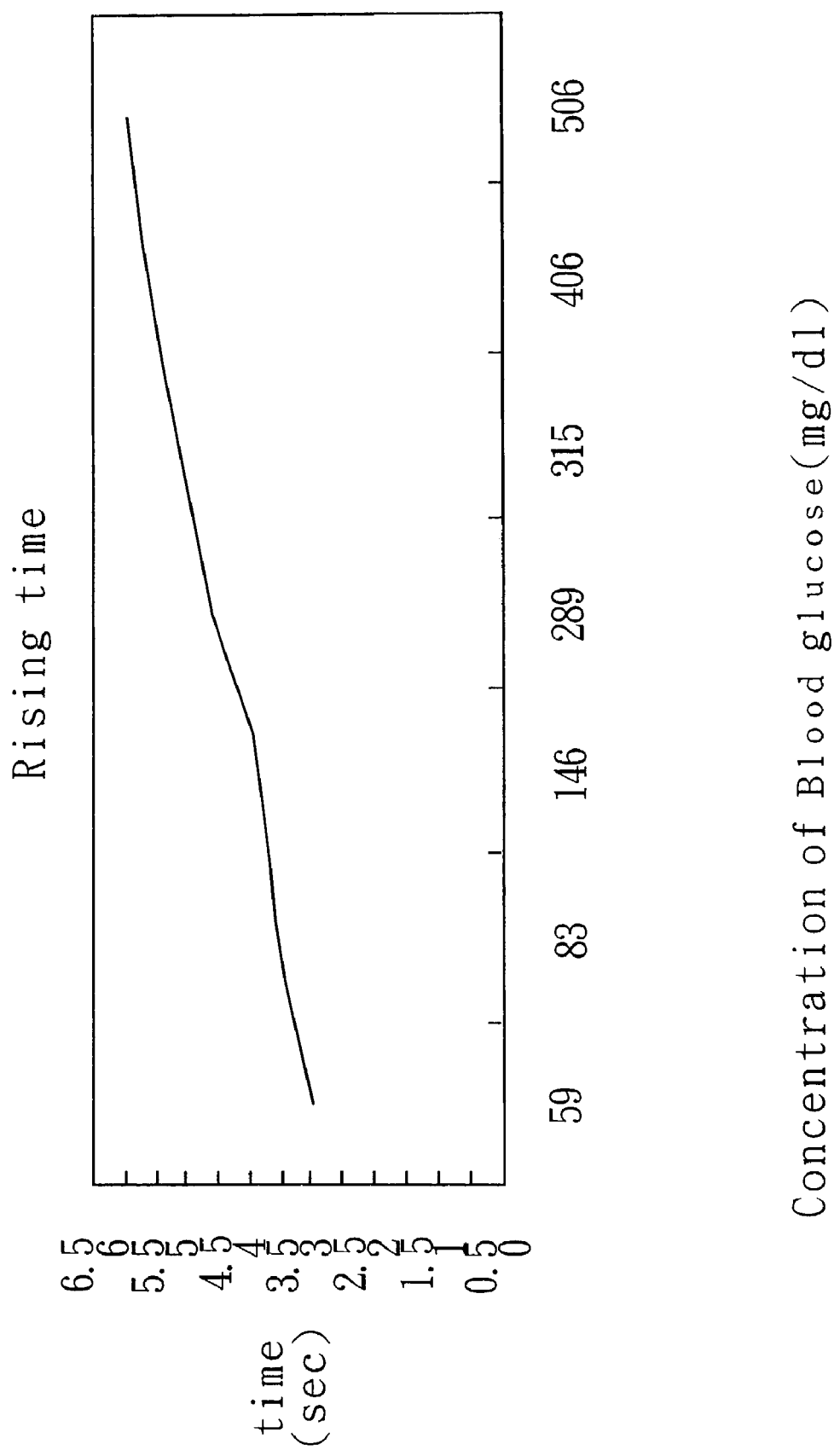
FIG. 4 is a schematic representation showing the relative diagram between the rising time and concentration of the blood glucose.

FIG. 4 is a relative diagram between the different concentration of the blood glucose and the rising time, wherein the x-coordinate is rising time, and the y-coordinate is voltage that expresses the concentration of the blood glucose. Thus, the unknown concentration of the blood glucose can be estimated by the relative diagram.

Although specific embodiments have been illustrated and described, it will be obvious to those skilled in the art that various modifications may be made without departing from what is intended to be limited solely by the appended claims.

What is claimed is:

1. A method for determining a concentration of blood glucose comprising:

providing a blood glucose solution on a test strip comprising an enzyme;

detecting a change in accumulation of a product of a chemical reaction occurring in response to said blood glucose solution on said test strip;

representing said change in accumulation of a product as an analog signal;

converting said analog signal to a digital signal;

converting said digital signal to a wave pattern having a first time and a second time, wherein the first time comprises an initial time and wherein the second time corresponds to a peak value;

calculating a difference value between said first time and said second time, wherein said difference value comprises a rising time of said wave pattern; and correlating a concentration of said blood glucose to said rising time.

2. The method of claim 1, wherein said chemical reaction comprises an oxidation-reduction reaction.

3. The method of claim 1, further comprising displaying said digital signal.

* * * * *